United States Patent [19]
Zimmon et al.

[11] Patent Number: 5,685,320
[45] Date of Patent: Nov. 11, 1997

[54] LATERAL BIOPSY DEVICE

[76] Inventors: David S. Zimmon, 7 Farm View Rd., Port Washington, N.Y. 11050; Rebecca Copenhaver Gibbs, 4900 Beaverdale Dr., Greensboro, N.C. 27406

[21] Appl. No.: 433,095

[22] Filed: May 3, 1995

Related U.S. Application Data

[63] Continuation of Ser. No. 261,982, Jun. 17, 1994, abandoned, which is a continuation of Ser. No. 754,750, Sep. 4, 1991, abandoned.

[51] Int. Cl.$^6$ .................................................. A61B 10/00
[52] U.S. Cl. .................................................. 128/754; 606/170
[58] Field of Search ........................... 128/754, 753, 128/752, 751, 749; 606/167, 170, 171, 159; 604/164, 170, 280, 284

[56] References Cited

U.S. PATENT DOCUMENTS

| | | | |
|---|---|---|---|
| Re. 33,258 | 7/1990 | Onik et al. | 604/22 |
| 1,167,014 | 1/1916 | O'Brien | 128/754 |
| 1,867,624 | 7/1932 | Hoffman | 128/754 |
| 2,505,358 | 4/1950 | Gusberg et al. | 128/754 |
| 3,837,345 | 9/1974 | Matar . | |
| 4,243,048 | 1/1981 | Griffin | 128/751 |
| 4,867,156 | 9/1989 | Stack et al. . | |
| 4,907,598 | 3/1990 | Bauer | 128/753 |
| 4,946,440 | 8/1990 | Hall | 604/95 |
| 5,085,659 | 2/1992 | Rydell | 606/47 |

FOREIGN PATENT DOCUMENTS

| | | |
|---|---|---|
| 1160573 | 9/1961 | Germany . |
| 125870 | 5/1959 | U.S.S.R. . |
| 175611 | 6/1965 | U.S.S.R. . |

*Primary Examiner*—Guy V. Tucker
*Attorney, Agent, or Firm*—Woodard, Emhardt, Naughton, Moriarity & McNett

[57] ABSTRACT

A lateral biopsy device for retrieving tissue samples atraumatically from remote locations within a patient's body. The biopsy device comprises an elongated flexible catheter which terminates at its distal tip in an annular cutting edge. Disposed within the central lumen of the catheter is an elongated flexible shaft which is somewhat longer than the catheter. An anvil having a rounded outer tip is securely attached to the distal end of the shaft. The anvil includes an annular surface that contacts the annular cutting edge of the catheter when the shaft is retracted with respect to the catheter. Gripping means attached to the proximal end of the shaft are also included to better enable the operator to advance and retract the anvil with respect to the annular cutting edge at the distal end of the catheter. A tissue sample positioned between the anvil and the distal end of the catheter is cut and removed when the annular surface of the anvil contacts the annular cutting edge of the catheter.

19 Claims, 3 Drawing Sheets

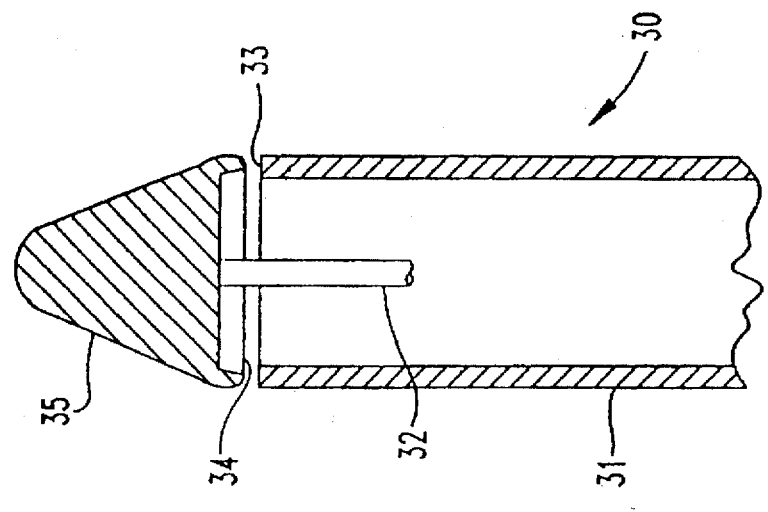
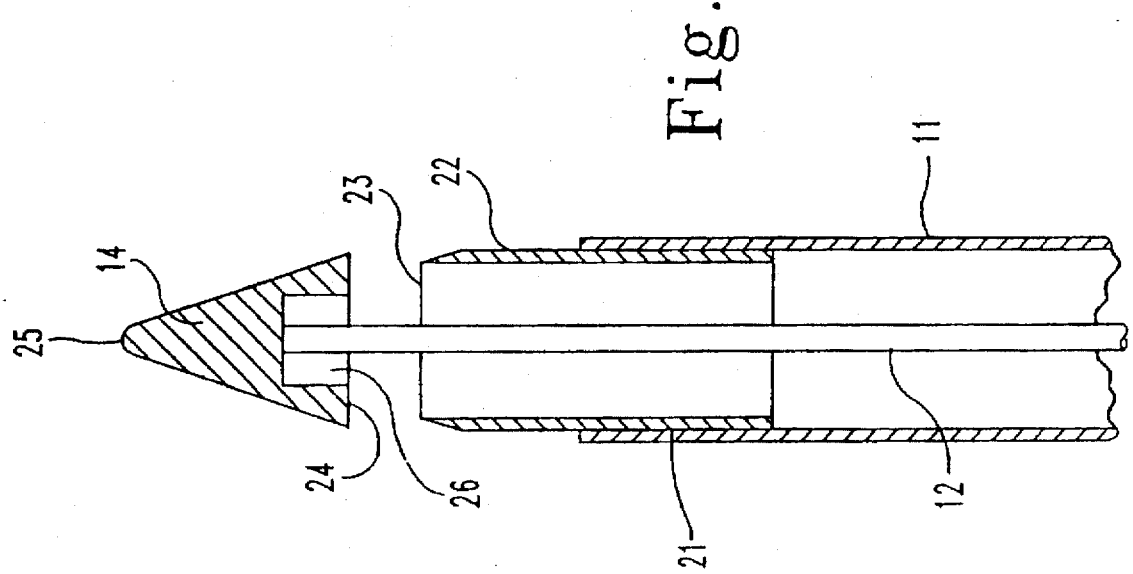

LATERAL BIOPSY DEVICE

CROSS REFERENCE TO RELATED APPLICATIONS

This application is a continuation of U.S. patent application Ser. No. 08/261,982 filed on Jun. 17, 1994 and entitled LATERAL BIOPSY DEVICE, now abandoned. The U.S. patent application Ser. No. 08/261,982 is a continuation of now abandoned U.S. patent application Ser. No. 07/754,750 filed on Sep. 4, 1991 and entitled LATERAL BIOPSY DEVICE, now abandoned.

BACKGROUND OF THE INVENTION

This invention relates generally to a method and device for performing biopsies or for removing fragments of tissue to relieve an obstruction in areas of stenosis. In particular, the invention relates to biopsy sampling or removing tissue in any remote luminal structure or cavity within a patient.

It is often necessary to obtain tissue samples for microscopic, chemical or bacteriologic analysis from deep within luminal structures that can only be approached by catheterization methods using endoscopic or fluoroscopic control, or on occasion blindly by palpitation. General methods and devices currently in use for biopsy include needles with hooks that allow the tearing of the tissue samples, sharpened needles that allow the cutting of fragments, and punch or grasping forceps that either cut or tear the samples. These devices all require pushing or pulling the device against the tissue to be sampled. Also, it is often difficult to position these biopsy devices adjacent to the area that must be sampled. The stiffness and shape of these devices make them difficult and often impossible to position or guide through a long and tortuous lumen in a patient, and particularly to bend the device around curves in the lumen.

What is needed is a biopsy device that is structurally simple but which obtains a tissue sample without pulling on the tissue to be sampled, and which includes a thin flexible body which enables the device to travel through nonlinear passageways within a patient to reach otherwise inaccessible locations.

SUMMARY OF THE INVENTION

A biopsy device for obtaining tissue samples from remote locations within a patient according to one embodiment of the present invention comprises a flexible catheter having a lumen, a distal end and a proximal end. A flexible shaft is slidably disposed within the lumen of the catheter. Finally, a cutting means is located near the distal end of the catheter. The cutting means is actuated to cut tissue when the flexible shaft is moved with respect to the catheter toward the proximal end of the catheter.

A method of performing a biopsy according to another aspect of the invention utilizing the above described device includes guiding the distal end of the catheter through a non-linear passageway within a patient until the cutting means of the device is adjacent the area where a tissue sample is to be removed. After the device is properly positioned within the patient, the cutting means is exposed to the tissue, thus allowing tissue to come into contact with the cutting means. Next, the shaft is retracted back toward the distal end of the catheter thereby actuating the cutting means to cut a tissue sample. Finally, the biopsy device is withdrawn from the patient's body and the tissue sample is removed from the distal end of the biopsy device for further analysis.

One object of the present invention is to provide an improved biopsy device for sampling and/or removal of tissue in any luminal structure or cavity within a patient.

Another object of the present invention is to provide an improved device and method for relieving obstructions in areas of stenosis within a patient.

Another object of the present invention is to provide a device which allows repetitive biopsies or scraping of tissue samples without the need to remove the device between samples.

Still another object of the present invention is to provide a less invasive method for obtaining tissue samples from remote locations within a patient.

Related objects and advantages of the present invention will be apparent from the following description.

BRIEF DESCRIPTION OF THE DRAWINGS

FIG. 2 is a sectional view of the distal end of the biopsy device shown in FIG. 1.

FIG. 3 is a sectional view of the distal end of the biopsy device according to another aspect of the present invention.

DESCRIPTION OF THE PREFERRED EMBODIMENT

Figure 1:
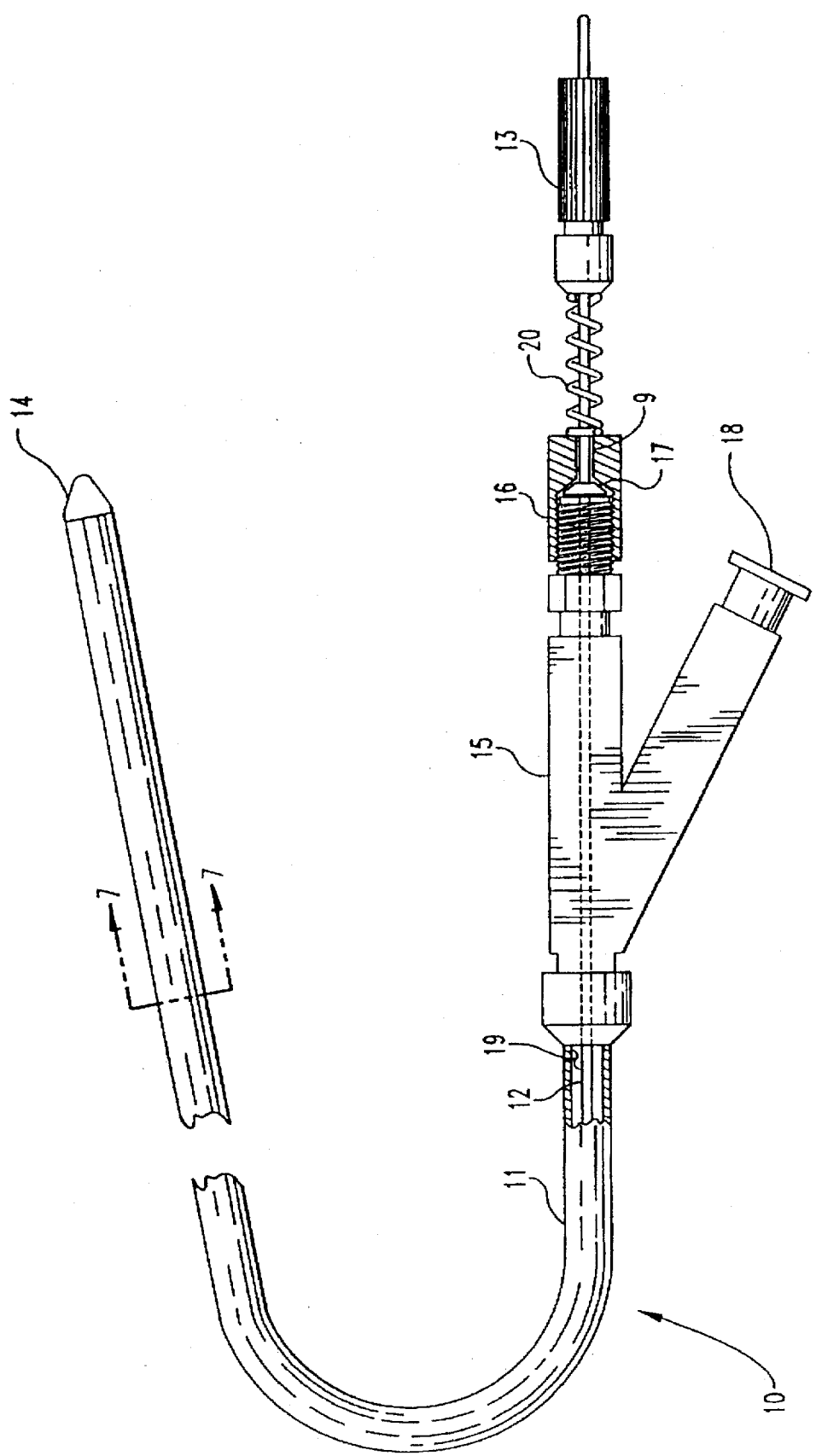
FIG. 1 is a partially sectioned side elevational view of a biopsy device according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1 shows a lateral biopsy device 10 according to one aspect of the present invention. The device includes an elongated flexible catheter 11 and an elongated flexible shaft 12 disposed within a central lumen 19 of catheter 11. Catheter 11 could range from a few to several hundred centimeters in length, depending upon the particular application. Attached to the proximal end of shaft 12 is gripping means 13. Gripping means 13 is shown as a releasable clamp but could equally well be any structure which permits the physician to advance and retract shaft 12 with respect to catheter 11. Attached to the distal end of shaft 12 is anvil 14. Anvil 14 may be attached by any suitable means such as by threaded engagement with shaft 12, adhesive, or by a welded connection. The diameter of shaft 12 is significantly smaller than central lumen 19 of catheter 11 in order that fluid may pass freely along the length of the central lumen of catheter 11. The proximal end of catheter 11 is connected to a standard Tuohy-Borst adapter 15 which is well known in the art and includes an injection-aspiration port 18. Nut 16 is attached to the proximal end of adapter 15 and compresses washer 17 in place to keep exit port 9 fluid-tight. In this way, any fluid injected, or suction applied, at port 18 acts through central lumen 19 and out the distal end of catheter 11.

When gripping means 13 is advanced toward nut 16, against the action of spring 20, the flexible shaft 12 advances within central lumen 19 and results in separating anvil 14 from the distal end of catheter 11. When gripping means 13 is released, spring 20 acts to automatically retract flexible shaft 12 back to its original position with anvil 14 once again in contact with the distal end of catheter 11. Biasing spring 20 is a desirable but not essential element to the proper functioning of the invention; without bias spring 20, the operator would simply have to manually retract anvil 14 by pulling backward on gripping means 13. Depending on the specific application, catheter 11 could be as small as one millimeter in diameter, but a typical size for the catheter is a 7 French catheter. Catheter 11 could be formed from any suitable flexible medical grade tubing material. Also, depending upon the application, catheter 11 could also be made to have variable stiffness along its length.

FIG. 2 depicts the distal end of the biopsy device shown in FIG. 1 after gripping means 13 has advanced shaft 12 with respect to catheter 11, thus separating anvil 14 from the distal end of catheter 11. Anvil 14 includes a smoothly rounded tip 25 which aids in the atraumatic insertion of the biopsy device, and an annular lower surface 24 which is remote from the rounded tip. Also shown is metal tube portion 22 which is attached to the distal end of catheter 11 at circumfrential location 21 by a suitable attachment means such as mating threads or adhesives. Tubular portion 22 includes an annular cutting edge 23 which extends beyond the distal end of catheter 11 and contacts annular surface 24 of anvil 14 when the anvil is retracted against the tubular portion 22. The word "annular" is meant to refer to any closed shape which includes but is not limited to circles, ellipses, and polygons. In this case, anvil 14 includes a cavity 26 which can serve to hold a portion of the tissue sample which is removed from the patient. Again, depending upon the particular application and the desired sample size, cavity 26 could be sized to a variety of volumes, or be eliminated altogether. Anvil 14 is preferably formed of medical grade stainless steel but could alternatively be formed of a radiopaque material, such as a platinum alloy, which would enable the physician to track the position of the device via x-rays during the catheter insertion procedure. It may also be desirable to inject radiopaque fluids out the distal end of the biopsy device to further aid the physician during the insertion procedure. This could be accomplished by injecting radiopaque fluids through port 18 of FIG. 1 while slightly separating the anvil from the distal tip of the catheter to permit the radiopaque fluid to escape into the patient.

FIG. 3 shows another embodiment of a biopsy device 30 according to another aspect of the present invention. While only the distal end of device 30 is shown, the remainder of the device is identical in configuration to the biopsy device 10 shown in FIG. 1. Biopsy device 30 includes a flexible elongated catheter 31, and a flexible elongated shaft 32 running through the central lumen of catheter 31. Attached to the distal end of shaft 32 is anvil 35. This device is different from the device shown in FIG. 2 in that the annular cutting edge 34 is included on the lower portion of anvil 35, and is received against the annular surface 33 on the distal tip of catheter 31. In FIG. 2, on the other hand, the annular cutting edge 23 is part of the distal tip of the catheter as opposed to part of the anvil 14.

Figure 4:
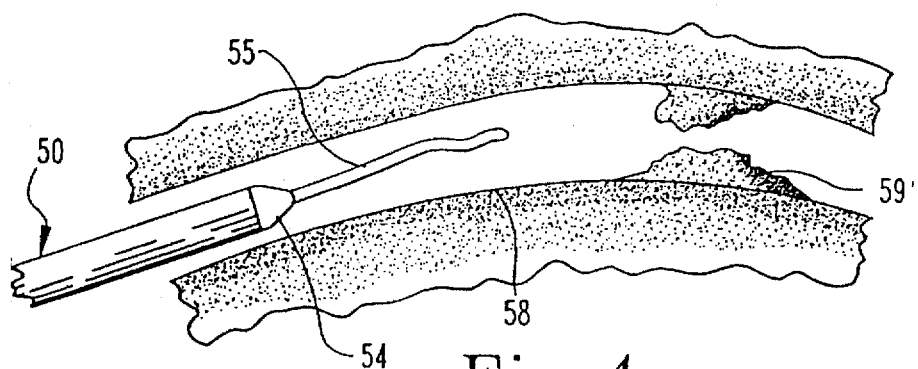
FIGS. 4-6 show a sequence using the biopsy device according to the present invention approaching and removing a tissue sample from within a patient.
Figure 5:
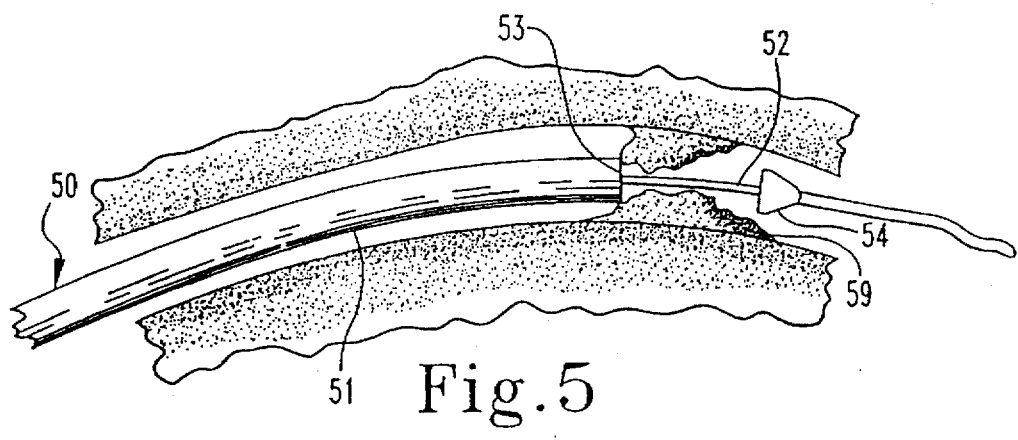
Figure 6:
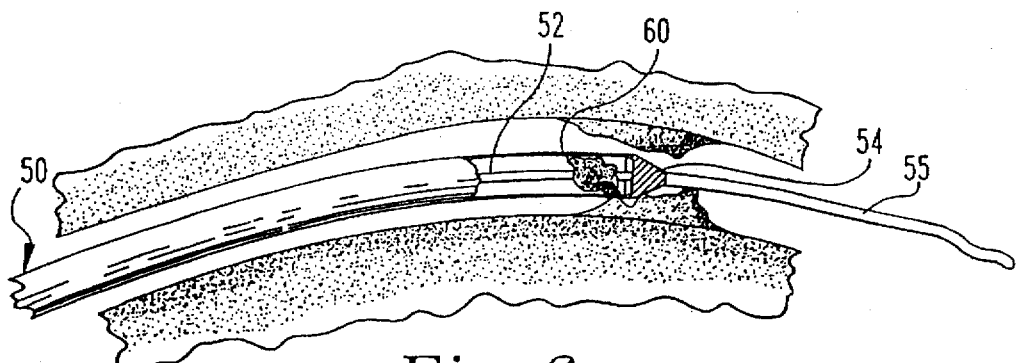

FIGS. 4–6 depict another embodiment of the present invention during the biopsy procedure within a patient. In this case, biopsy device 50 includes a filiform wire guide tip 55 extending distally from the anvil 54 in order to aid the physician during the catheter insertion procedure, but which is otherwise identical to the device of FIG. 1. Guide tip 55 typically ranges in length from one to fifteen centimeters in length, but could be outside this range depending upon the particular application. Guide tip 55 could also include a radiopaque element to aid the physician during the insertion procedure. FIG. 4 shows the biopsy device 50 being advanced through a portion of a non-linear passageway 58 within a patient toward a tissue growth 59 which is desired to be sampled. FIG. 5 shows the biopsy device 50 after it has arrived at the desired location and after the anvil 54 has been separated from the distal tip 53 of catheter 51 in order to draw in a portion of the tissue 59 to be sampled. The cutting means of the device are thereby exposed to the tissue when anvil 54 is separated from the distal end of the catheter. In order to increase the size of a tissue sample taken, suction can be applied though the central lumen of the catheter 51 via an aspiration port located at the proximal end of the catheter, such as port 18 shown in FIG. 1. The size of the biopsy sample is determined by a number of independently controllable factors including the separation distance of the anvil from the catheter before cutting, the diameter of the central lumen of the catheter, the diameter of the shaft, the size of any cavity that may exist on the underside of the anvil, and the vacuum or suction level utilized during the cutting procedure. It may also be desirable to include calibration marks, such as the marks 8 shown in FIG. 1, on the proximal end of the biopsy device so that the physician can precisely determine and control the separation distance between the anvil and the catheter during the cutting procedure.

FIG. 6 shows biopsy device 50 after a tissue sample 60 has been removed. Tissue sample 60 is removed by retracting shaft 52 thereby positioning anvil 54 against the distal tip 53 of catheter 51. The tissue sample 60 is cut when the annular surface of anvil 54 is forced into contact with the annular cutting edge 53 of the distal tip of catheter 51. After removing the tissue sample 60 from the tissue area 59, the biopsy device 50 is withdrawn from the patient. However, if a larger tissue sample is required, or if the device is being used to remove a stenosis from a lumen within a patient, then the steps shown in FIGS. 5 and 6 are repeated as necessary before withdrawing the biopsy device from the patient.

Figure 7:
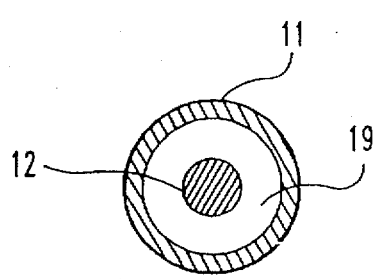
FIG. 7 is a cross-section view of the device of FIG. 1 looking in the direction of the arrows labeled A.
Figure 8:
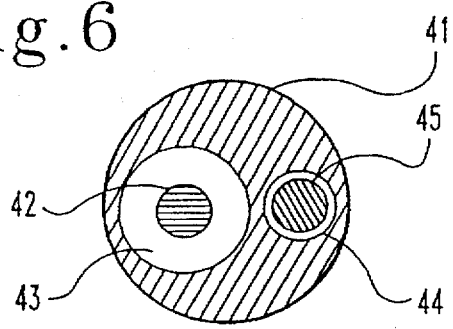
FIG. 8 is a cross-section of a two-lumen catheter according to another aspect of the present invention.

FIG. 7 shows a cross-section of the biopsy device 10 shown in FIG. 1 looking in the direction of the arrows labeled A. As can be seen, central lumen 19 of catheter 11 is significantly larger than the diameter of shaft 12 thereby allowing fluids to pass freely through central lumen 19 adjacent to shaft 12. FIG. 8 shows a cross-section of still another embodiment of the present invention in which a dual lumen catheter 41 is used in place of the single lumen catheter shown in the earlier figures. In this case, first lumen 43 includes a flexible shaft 42 which is functionally analogous to the shaft 12 shown earlier. Also shown is a second lumen 44 which receives a wire guide 45. In this embodiment, the biopsy device is used by first positioning the wire guide 45 within the patient adjacent to the area to be sampled. After wire guide 45 is properly positioned, the biopsy device is threaded over the wire guide by threading lumen 44 over wire guide 45, and then advancing the biopsy device over the wire guide 45 until the distal end of the biopsy device is adjacent the tissue to be sampled. Wire guide 45 may be withdrawn after the biopsy device is in place, or wire guide 45 may be left in place after the biopsy device has been used and subsequently withdrawn from the patient. In this way, the physician could obtain a biopsy prior to placing a stent or performing a balloon dilation. Also, the biopsy device could be used after a balloon dilation in order to remove any remaining stenosis from the dilated lumen.

Biopsy devices according to the above invention could be made for repeated use or could be made disposable for single use only. Also, because the anvil normally is closed against the distal end of the catheter while the device is being withdrawn from the patient, the bacteriologic sample could be retrieved and submitted for culture analysis without risking contamination of the sample by unnecessary contact with other tissues within the patient, or other contaminated matter. Another feature which could be added to the invention would be to supply electric current to the cutting means so that the surrounding tissue is cauterized after a tissue sample has been removed.

While the invention has been illustrated and described in detail in the drawings and foregoing description, the same is to be considered as illustrative and not restrictive in character. For instance, the invention can be used in a myriad of locations within a patient including blood vessels, the urinary tract, the gastrointestinal tract, the esophagus or small intestine, the lungs, or any other non-linear passageway such as a fistula or a cavity. The invention is also equally applicable to veterinary medicine. It being understood that only the preferred embodiments have been shown and described and that all changes and modifications that come within the spirit of the invention are desired to be protected.

I claim:

1. A biopsy device comprising:

an elongated flexible catheter having a proximal end and an opposite other distal end, said catheter having a substantially unobstructed lumen extending from said proximal end to said distal end;

a flexible shaft slidably disposed within said lumen, said flexible shaft having a proximal end and an opposite other distal end;

an anvil connected to said distal end of the flexible shaft, said anvil having a smoothly rounded outer surface, said outer surface extending distally from said distal end of said catheter for aiding in the atraumatic insertion of the biopsy device;

said lumen having a diameter significantly larger than said shaft extending from said proximal end to said distal end for passing materials through said lumen adjacent said shaft; and cutting means for cutting tissue near said distal end of said catheter, said cutting means being actuated when said shaft is moved axially relative to said catheter toward said proximal end of said catheter.

2. The biopsy device of claim 1, wherein said lumen passing material in a substantially annular pathway around said shaft.

3. The biopsy device of claim 2 wherein said cutting means includes a cutting edge connected to one of said shaft and said anvil, and further including a cutting surface connected to the other of said shaft and said anvil, wherein upon cutting tissue said cutting edge and said cutting surface substantially abutting.

4. The biopsy device of claim 3 which further includes a spring for spring biasing said shaft toward said proximal end of said catheter to maintain said cutting edge in contact with said cutting surface, said spring positioned external of said lumen for minimizing obstructions within said lumen.

5. The biopsy device of claim 4 which further includes a fluid communication port for the passage of fluids into and out of said lumen, said port being located near said proximal end of said catheter and remote from said distal end of said catheter.

6. The biopsy device of claim 5 wherein:

said anvil includes a second surface opposite said smooth outer surface and normally disposed proximate said distal end of said catheter;

said cutting surface is formed on said distal end of said catheter, and wherein said cutting edge is formed on said second surface of said anvil.

7. The biopsy device of claim 6 wherein said anvil includes a wire guide leader connected thereto and extending distally therefrom, said wire guide leader formed of a radiopaque material, and wherein said anvil formed of a radiopaque material.

8. The biopsy device of claim 7 wherein said catheter further includes a second lumen adjacent said first lumen for receiving a wire guide therethrough.

9. The biopsy device of claim 5 wherein:

said anvil includes a second surface opposite said smooth outer surface of said anvil; and said cutting means includes an annular cutting edge connected to said distal end of said catheter and a cutting surface connected to said second surface of said anvil, said annular cutting edge and said cutting surface being normally abutting.

10. The biopsy device of claim 9 wherein said anvil includes a wire guide leader connected thereto and extending distally therefrom, said wire guide leader formed of a radiopaque material, and wherein said anvil formed of a radiopaque material.

11. The biopsy device of claim 10 wherein said catheter further includes a second lumen adjacent said first lumen for receiving a a wire guide therethrough.

12. A biopsy device comprising:

a flexible catheter having a proximal end and an opposite other distal end, said catheter having a lumen extending from said proximal end to said distal end;

a flexible shaft having a proximal end and an opposite other distal end, said shaft being slidable within said lumen;

said lumen defining a primary fluid communication passageway adjacent and along said shaft for the passage of materials, said lumen being significantly larger than said shaft and extending from said proximal end to said distal end; and an anvil connected to the distal end of said flexible shaft, said anvil having a rounded outer end extending outwardly from the distal end of said catheter for aiding in the atraumatic insertion of the biopsy device; and cutting means for cutting tissue near the distal end of said catheter, said cutting means being actuated upon relative axial movement between said shaft and said catheter.

13. The biopsy device of claim 12, which further includes a spring for biasing said shaft toward the proximal end of said catheter, said spring being positioned outside of the lumen to prevent obstructing said primary fluid communication pathway.

14. The biopsy device of claim 13 wherein said cutting means includes a cutting edge connected to one of said shaft and said anvil, and further including a cutting surface connected to the other of said shaft and said anvil, wherein upon cutting tissue said cutting edge and said cutting surface substantially abutting one another.

15. The biopsy device of claim 14 which further includes a fluid communication port for the passage of fluids into and out of said lumen, said port being located near said proximal end of said catheter and remote from said distal end of said catheter.

16. The biopsy device of claim 15 wherein:

said anvil includes a second end opposite said rounded outer end and normally disposed proximate said distal end of said catheter; and said cutting surface being formed on said distal end of said catheter, and wherein said annular cutting edge is formed on said end of said anvil.

17. The biopsy device of claim 16 wherein said catheter further includes a second lumen adjacent said first lumen for receiving a wire guide therethrough, said anvil includes a wire guide leader connected thereto and extending distally therefrom, said wire guide leader formed of a radiopaque material, and wherein said anvil formed of a radiopaque material, and further including a second lumen adjacent said first lumen for receiving a a wire guide therethrough.

18. The biopsy device of claim 15 wherein:

said anvil includes a second end opposite said rounded outer end of said anvil; and said cutting means includes an annular cutting edge connected to said distal end of said catheter and a cutting surface connected to said second end of said anvil, said annular cutting edge and said cutting surface being normally abutting.

19. The biopsy device of claim 18 wherein said catheter further includes a second lumen adjacent said first lumen for receiving a wire guide therethrough, said anvil includes a wire guide leader connected thereto and extending distally therefrom, said wire guide leader formed of a radiopaque material, and wherein said anvil formed of a radiopaque material, and further including a second lumen adjacent said first lumen for receiving a a wire guide therethrough.

* * * * *